United States Patent [19]

Cobia et al.

[11] Patent Number: Plant 7,201

[45] Date of Patent: Mar. 20, 1990

[54] PLANT OF THE CACTACEAE PLANT FAMILY 'CAMBRIDGE'

[75] Inventors: Barnell L. Cobia, Winter Garden; Mark E. Cobia, Orlando, both of Fla.

[73] Assignee: B. L. Cobia, Inc., Winter Garden, Fla.

[21] Appl. No.: 284,322

[22] Filed: Dec. 13, 1988

[51] Int. Cl.[4] ..... A01H 5/00

[52] U.S. Cl. ..... Plt./88

[58] Field of Search ..... Plt./88

*Primary Examiner*—James R. Feyrer

*Attorney, Agent, or Firm*—Roger L. Martin

[57] ABSTRACT

A new and distinct plant variety of the Cactaceae family is of the type known commercially as a "Christmas Cactus" and has a growth habit which is similar to that the "Gold Charm" variety (U.S. Plant Pat. No. 5,104) but which, nevertheless, differs, among other things, by having phylloclades with thicker and wider wings and thicker teeth in greater numbers per phyllocalde, and flowers which are sterile and have shorter tube laminating tepals, a perianth tube with longer major and minor elliptical axis, shorter tube attached stamens and larger diameter and shorter length styles.

4 Drawing Sheets

BACKGROUND OF THE INVENTION

The invention relates to a new and distinct plant variety of the Cactaceae family and which has been named the *Zygocactus truncatus* 'Cambridge' by the inventors.

Certain plant varieties of the Cactaceae family are well known in the foliage plant market and among these are those which are commonly referred to as the Christmas Cactus varieties because they tend to bloom during the Thanksgiving-Christmas holiday season in the northern hemisphere.

The Christmas Cactus varieties on the market have blooms which vary in color from one variety to the next as is evident from the current U.S. patent art. One of the more popular varieties sold commercially in the market place in the variety that has been named *Zygocactus truncatus* 'Gold Charm'. This variety is the only Christmas Cactus in the market place which is known to the inventors as having a generally yellow colored bloom. It forms the subject matter of U.S. Plant Pat. No. 5,104.

SUMMARY OF THE INVENTION

A general objective has been to develop a new plant variety with a white colored bloom and which is distinguishable from the patented "Gold Charm" variety and which is capable of being marketed in competition therewith.

The objective has been fully realized by the development of the new plant variety hereinafter described in detail. The new plant variety was developed in a nursery located at Winter Garden, Fla., from a natural mutation that appeared on a specimen of the "Gold Charm" variety which was under cultivation at the nursery.

Through successive propagations of cuttings taken from the mutatred plant part, it has been ascertained that specimens of the new plant variety generally resemble the "Gold Charm" variety in most respects but are distinguishable from this variety and from other related varieties known to the inventors by a growth habit which is evident in plant specimens of the new variety that have been propagated and grown under nursery conditions utilized in the growing of tropical plants in Winter Garden, Fla., as combining the following principal characteristics:

1. A more erect posture at maturity than the "Gold Charm" variety.

2. Phylloclades which, in comparison to the "Gold Charm" variety, have (a) wings with generally greater thickness and width dimensions, and (b) teeth with generally greater thickness dimensions and in a larger number per phylloclade, 3. Flowers which, in comparison to the "Gold Charm" variety, are sterile and have (a) a sepaloid tepal series with generally shorter length dimensions, (b) a tube laminating tepal series that has a larger number of tepals, (c) a perianth tube that at the throat has a generally longer major elliptical axis dimension and a generally longer minor elliptical axis dimension, (d) an androecium with filaments of the tube attached stamen group that have shorter length dimensions, (e) a gynoecium that has a style with a generally shorter length dimension and generally larger diameter and ovaries with generally longer minor axis dimensions at the distal end of the concavity.

BRIEF DESCRIPTION OF THE DRAWINGS

The accompanying drawings serve by color photographic means to illustrate the new plant variety and wherein one sheet show a eight (8) month old specimen which was grown from the propagation of a single phylloclade in a conventional 3 in. pot found in the marketplace. A second sheet shows an enlargement of a fully open bloom taken from the specimen shown in the first mentioned sheet. Still another sheet shows another fully open bloom together with a bloom as sectioned generally longitudinally through the perianth tube and ovary to expose the style and stamen arrangement. The last sheet show three phylloclades taken from a specimen of the new variety, each phylloclade having an attached bud or bloom to illustrate the buds in progressive stages of maturity.

DETAILED PLANT DESCRIPTION

The following is a detailed description of the new plant variety with colors and hues, unless otherwise clearly indicated by the text, as, for example, through the absence of color notations, being named in accord with the I.S.C.C.-N.B.S. Method of Designating Colors (U.S. Dept. of Commerce, National Bureau of Standards, Circular 553), the named colors being interpreted from color notations derived by comparison with color specimens of the Munsell Book of Color. The description is further based on observations of well fertilized plants about one year old from initial propagation and which were grown under 50–75% shaded glasshouse nursery conditions in the Winter Garden, Fla. area and wherein temperatures range from 60°–85° F. during the winter months, from 75°–95° F. during the summer months, and are ambient during the intervening periods.

I. Name: *Zygocactus truncatus* 'Cambridge'.

II. Parentage: This variety was developed from a natural mutation that occurred on a specimen of the variety known as *Zygocactus truncatus* 'Gold Charm' (See. U.S. Plant Pat. No. 5,104).

III. Classification:

*Botanic* (*Britton and Rose, The Cactaceae,* Constable and Co., Ltd., London 1937, Vol. IV).—(1) Family: Cactaceae. (2) Tribe: Cereeae. (3) Sub-Tribe: Epiphyllanae. (4) Genus: Zygocactus. (5) Species: *truncatus* (Haworth) Schumann.

*Commercial.*—Thanksgiving–Christmas blooming cactus.

IV. Form: Epiphylic and terrestrial shade loving, succulent, leafless plant with jointed and branched stems.

V. Stems:

A. *General.*—Irregular with usually multichotomous branching of both upright and pendulous, adventitiously rootable, flattened phylloclades that have a prominent midrib and prominently toothed lateral wings.

B. *Phylloclades.*—(1) General: Elongated and flat with a transversely elongated, areole bearing, truncated apex, with inwardly tapering basal wing margins that merge with a usually broadly pointed basel juncture with the phylloclade therebelow, and with an axially located areole usually being associated with each tooth. (2) Midrib: (a) General — Extends longitudinally of phylloclade and continuously through joints and with a laterally tapering cortex at the wing insertions. Pith surrounding vascular bundles that branch and provide lateral extensions of the vascular system to the marginal teeth. (b) Texture — Smooth, waxy epidermis with wax in small embedded scales and becoming woody in basal stem areas with specimen againg. (c) Size (at maturity) — 1. Length: Usually 33–57 mm. 2. Thickness: Usually 3–7 mm. (d) Color (at maturity) — Usually dominated by a yellow green hue. Commonly moderate yellow green (5 GY 5/6) (7.5 GY 5/6). (3) Wings: (a) General — Dentate and generally flattened from midrib cortex to tooth insertions and with slight thinning taper toward margins. (b) Margins — Toothed. (c) Texture — Succulent to leathery with smooth, waxy epidermis where the wax is arranged in small embedded scales of higher density than in midrib area, and becoming corky in the basal stem areas with specimen aging. (d) Size (at maturity) — 1. Thickness: About 1.5–3 mm in the area intermediate the margin and midrib. 2. Width: Usually 10–22 mm as measured from phylloclade axis to most offset lateral areole. (e) Color (at maturity) — Usually dominated by an olive green and/or yellowish green hue. Commonly moderate olive green (7.5 GY 3/4) (7.5 GY 4/6) and/or dark yellowish green (10 GY 3/4). (4) Teeth: (a) Shape — 1. General: Generally flattened and tapering along the margins from the insertion in the wing to an apex that has a hyaline, single cell, pointed spine with nonpredictable bending. 2. Adaxial margin: Usually straight to convex. 3. Abaxial margin: Usually straight to concave. (b) Orientation — Generally project distally of phylloclade in an alternate arrangement. (c) Margins — Entire. (d) Texture — Succulent to leathery with smooth waxy epidermis having wax in small embedded scales of density comparable to wings, and becoming corky in basal stem areas with specimen aging. (e) Size (at maturity) — 1. Thickness: Usually 1–3 mm in center area. 2. Areole to apex dimension (adaxial marginal side): Usually 2.5–12 mm in the upper quadrants of the phyllocalades. (f) Number — Usually 7–10 per phylloclade. (g) Color — Usually dominated by an olive green and/or yellow green hue. Commonly moderate olive green (7.5 GY 3/4) and/or moderate yellow green (5 GY 5/6). (5) Areoles: (a) Terminal areole — Large, elongated, oval shaped with several acicular bristles, and several buds that may mature into either new phylloclades or flowers. The opposite ends of the areole are located adjacent to subsidiary areoles which are, in turn, located at the axils of the teeth at the distal end of the phylloclade. (b) Axillary areoles — Acicular bristles without glochidia but having copious, short, brownish, multicellular, wooly hairs. In areoles located below the teeth at the distal end of the phylloclade, there is usually only one areole which is frequently latent.

VI. Buds: Unarmored, ovid and chlorophyllous.

VII. Flowers:

A. *General.*—Sessile, zygomorphic, usually solitary, terminal, perfect and epigynous with double hypanthium and whorled tepals (undifferentiated sepals and petals) having a spiral emergence as a perianth provided with a sepaloid series of free tepals, a tube laminating series of tepals, and a tube forming series of united tepals.

B. *Sepaloid tepal series.*—(1) General: Free tepals inserted on top of ovary. (2) Shape: Deltoid in outer members of whorl and grading inwardly in the whorl to provide progressively greater length dimensions and broader apices. All members have a pointed tip and entire margins with sparse irregular teeth appearing mainly in the apex areas of the inner members of the whorl. (3) Texture: Succulent and glabrous outer whorl members and grading inwardly in whorl to silken blades with fleshy basal areas. (4) Number: Usually 4–7. (5) Size (at full bloom): (a) Length (base-tip dimension) — Usually less than 15 mm. (b) Width (maximum) — Usually less than 13 mm. (6) Color (at full bloom): Varies from the outer members to the inner members with the smallest outer whorl tepals usually having a continuous field that in color is dominated by a yellow green hue. The inner whorl tepal members have marginal and center blade areas that in color are dominated by a yellow green and/or yellow hue that projects proximally to merge with the distally projecting white basel area color. Commonly strong yellow green (2.5 GY 7/8) (2.5 GY 6/8) and/or moderate yellow green (2.5 G Y 5/6) in the continuous field of the smallest outer whorl member. Commonly brilliant yellow green (2.5 GY 8/8), strong yellow green (2.5 GY 6/8) (2.5 GY 7/8) and/or pale yellow (2.5 Y 9/4) in the marginal and center blade areas of the inner whorl members and strong yellow green (2.5 GY 7/8) (2.5 GY 7/8) and/or brilliant yellow green (2.5 GY 8/8) in the basal areas of the outer whorl members. (7) Orientation: Erect to recurve at full bloom.

C. *Tube laminating tepal series.*—(1) General: Tepals inserted on ovary and basally united below the throat as outer laminations on the perianth tube and with progressively greater amount of basal fusion inwardly in the whorl. (2) Shape: Zygomorphic and grading inwardly in the whorl with progressively greater length dimensions and broader apices so that the blade area changes inwardly in the whorl from ovate with an acute tip to ovate with a rounded tip. Margins entire to fimbriolate with sparse, irregular teeth mainly in apex areas. (3) Texture: Succulent and glabrous outer whorl members and grading inwardly to silken blades with slightly fleshy basal areas. (4) Number: Usually 6–11 tepals. (5) Size (at full bloom): (a) Length (base-tip dimension) — Usually ranging from about 10 to about 55 mm. (b) Width (maximum) — Usually ranging from about 6 to about 19 mm. (6) Color (at full bloom): (a) General — Tepals with basal areas which in the outer whorl members are in color dominated by a yellow green hue immediately above the insertion and which is the inner whorl members are white in color immediately above the insertion. The marginal and center blade areas are in color dominated by a yellow hue and the color extends proximally to merge with the distally extending color in the basal area of the tepal. (b) Basal area — Commonly brilliant yellow green (2.5 GY 9/8) in the outer whorl members and translucent white in the inner whorl members. (c) Blade area — Commonly light yellow (2.5 Y 9/6) (near 2.5 Y 8/8), brilliant yellow (near 2.5 Y 8/8), moderate yellow (near 2.5 Y 8/8) and/or strong yellow (2.5Y8/8) in the marginal and center blade areas. (7) Orientation: Perpendicular to recurve at full bloom.

D. *Tube forming tepal series.*—(1) General: Tepals basally united to form hollow perianth tube that is inserted on ovary and equipped at its throat with an irregular carina (keel). (2) Shape: (a) Perianth tube — Elongated and elipsoidal in cross section with the major ellipsoidal axis usually generally normal to the plane of the supporting phylloclade. (b) Blades — Nearly zygomorphic and thinly spatulate with acute tips and entire margins having sparse irregular teeth in apex area. (c) Carina (keel) — Irregular and transcending. (3) Texture: (a) Perianth tube — Thick, succulent and slightly ribbed. (b) Blades — Translucent and silken. (c) Carina (keel) — Fleshy. (4) Number: Usually 8–9. (5) Size (at full bloom): (a) Perianth tube — 1. Length (base-keel): Usually 30–40 mm along tube axis. 2. Major Axis: Usually 12–20 mm at throat interior. 3. Minor axis: Usually 9–12 mm at throat interior. (b) Blades — 1. Length (keel-tip): Usually 29–35 mm. 2. Width (maximum): Usually 13–18 mm. (6) Color (at full bloom): (a) Perianth tube — A basic field that is translucent white with longitudinally extending, randomly arranged striations or streaks that, in color, are commonly purplish white (5 RP 9/1) and/or pale purplish pink (5 RP 9/2). The basic field is commonly white (2.5 GY 9.5/0). (b) Blades — A continous marginal and center blade area that is nearly uniform in color distally of the keel, the color being usually dominate by a yellow hue. Commonly light yellow (near 2.5 Y 8/8) (2.5 Y 9/6), brilliant yellow (near 2.5 Y 8/8), moderate yellow (near 2.5 Y 8/8), and/or strong yellow (near 2.5 Y 8/8) in the marginal and center blade areas. Commonly white (2.5 Y 9.5/0) with occasional streaks or striations of purplish white (5 RP 9/1) and/or pale purplish pink (5 RP 9/2) near keel. (c) Carina (keel) — Color usually dominated by a purplish pink hue. Commonly deep purplish pink (5 RP 6/10). (7) Orientation: Acute to recurve.

E. *Androecium (stamens).*—(1) General: Numberous exserted and diadelphous stamens with one group having filaments basally fused to the perianth tube and the other group having filaments basally united to form a nectary housing, thin annulus around the style and which is provided with a thin, deflexed, irregular, toothed margin or ruffle at the throat of the annulus. (2) Stamen number: (a) Tube attached group — Usually 73–103. (b) Basally united group — Usually 17–24. (3) Filaments: (a) General — Translucent with anther connective. (b) Shape — Long, slender, terete. (c) Texture — Glabrous and capillaceous. (d) Color — Usually translucent white over entire length. (e) Size (at full bloom) — 1. Length: a. Tube attached group — Usually 26–67 mm. b. Basally united group — Usually 40–56 mm. 2. Diameter: Usually about 0.5 mm at insertion and tapering to about 0.25 mm at distal end. (4) Anthers: (a) General — Adnate with four longitudinally dehiscent pollen sacs and connective inserted at end. (b) Shape — Elongated. (c) Texture — Waxy. (d) Color (before dehiscence) — Dominated by a greenish yellow hue. Commonly pale greenish yellow (10 Y 9/4) and/or light greenish yellow (10 Y 9/6). (e) Sterility — Sterile.

F. *Gynoecium (pistil).*—(1) General: Exserted with compound, pariental placentation and united style surrounded by annular diffuse yellowish nectary at its insertion. (2) Style: (a) General — Hollow, stout and inserted at ovary. (b) Shape — Elongated and terete. (c) Texture — Fleshy and smooth. (d) Color — Usually dominated by a reddish purple hue and progressively varying in color between basal and distal ends. Commonly strong reddish purple (2.5 RP 4/10) at basal end and deep reddish purple (2.5 RP 3/10) at the distal end. (e) Size (at full bloom) — 1. Length: Usually 57–65 mm. 2. Diameter: Usually 1.5–2.0 mm intermediate opposite ends. (3) Stigma: (a) General — Exserted and erect with usually 6–8 inner marginally adhering lobes. (b) Shape —

Elongated and tapered toward lobe tips and having relatively blunt apices. (c) Texture — Fleshy and smooth with inner sides of lobes having short glutinous capillaceous hairs. (d) Color — Usually dominated by a reddish purple hue. Commonly light reddish purple (2.5 RP 6/8) and/or strong reddish purple (2.5 RP 5/10). (e) Size — 1. Length: Usually 4–7 mm along inner margins. (4) Ovary: (a) General — Inferior with thin epidermis and usually 6–8 carpules with numerous ovules. (b) Shape — Terete to ovoid and generally broadening from insertion to floral end. Ribbed single concavity with inserted style. (c) Texture — Succulent with glabrous thin outer epidermis. (d) Color — A basic field with color usually dominated by a yellow green hue. Commonly moderate yellow green (5 GY 5/6) and/or strong yellow green (5 GY 6/8). (e) Size — 1. Length: Usually 8–11 mm from insertion to cavity base. 2. Major axis: Usually 9–12 mm at distal end of concavity. 3. Minor axis: Usually about 8–10 mm at distal end of concavity.

VIII. Growth Habit: Erect.

GENERAL DESCRIPTION OF A PLANT SPECIMEN

Age of plant: Nine (9) months from initial propagation of single phylloclade.

Branches from propagated phylloclade: Two (2).

Total number of new phylloclades grown: Ten (10).

General:

| Branch No. | No. of Phylloclades | Maximum Branch Length | No. of Tips |
|---|---|---|---|
| 1 | 4 | 201 mm | 1 |
| 2 | 6 | 202 mm | 2 |

Midribs:

| Branch No. | Average Midrib Length | Average Midrib Thickness |
|---|---|---|
| 1 | 50.3 mm | 4.4 mm |
| 2 | 49.7 mm | 4.0 mm |

Wings:

| Branch No. | Average Wing Center Thickness | Average Wing Width (Maximum) |
|---|---|---|
| 1 | 2.6 mm | 18.0 mm |
| 2 | 2.4 mm | 17.3 mm |

Teeth:

| Branch No. | Teeth (Avg.) per Phylloclade | Avg. Tooth Center Thickness | Avg. Aerole/ Apex Length |
|---|---|---|---|
| 1 | 9.5 | 1.4 mm | 7.5 mm |
| 2 | 9.2 | 1.4 mm | 6.1 mm |

Phylloclade color: Moderate yellow green (7.5 GY 5/6) (5 GY 5/6) and moderate olive green (7.5 GY 3/4) (7.5 GY 4/6).

GENERAL DESCRIPTION OF A FLOWER

The following is a general description of a flower of the new plant variety and which bloomed in December on an 8 month old plant specimen grown under shaded greenhouse nursery conditions in Winter Garden, Fla., U.S.A.

No. of buds and blooms on plant specimen: 4.

Bloom life: 8 days.

Sepaloid tepal series:

*Number.*—5.

*Tepal size (at full bloom).*—Maximum base-tip dimension: 13 mm. Minimum base-tip dimension: 4 mm. Maximum width dimension: 12 mm.

*Color (at full bloom).*—Strong yellow green (2.5 GY 7/8) (2.5 GY 6/8) and brilliant yellow green (2.5 GY 8/8) in the continuous field of the small outer whorl tepal members. Pale yellow (2.5 Y 9/4) in the marginal and center blade areas and brilliant yellow green (2.5 GY 8/8) and strong yellow green (2.5 GY 6/8) (2.5 GY 7/8) in the basal areas of the inner whorl members.

Tube laminating tepal series:

*Number.*—9.

*Size (at full bloom).*—Maximum base-tip dimension: 52 mm. Minimum base-tip dimension: 11 mm. Maximum blade width: 18 mm. Minimum blade width: 8 mm.

*Color.*—Light yellow (2.5 Y 9/6) (near 2.5 Y 8/8), brilliant yellow (near 2.5 Y 8/8), moderate yellow (near 2.5 Y 8/8) and strong yellow (near 2.5 Y 8/8) in marginal and center areas of the blades and brilliant yellow green (2.5 GY 9/8) and white in the basal areas of the blades.

Tube forming tepal series:

*Number.*—8.

*Size (at full bloom).*—Periant tube: Length (base to keel) — 38 mm along tube axis. Major axis — 18 mm at throat interior. Minor axis — 11 mm at throat interior. Blades: Maximum length (keel-tip) — 33 mm. Mininum length (keel-tip) — 31 mm. Maximum blade width — 18 mm. Minimum blade width — 16 mm.

*Color.*—Perianth tube: A basic field that is generally white (2.5 GY 9.5/0) with random striations of purplish white (5 RP 9/1). Blades: White (2.5 GY 9.5/0) in basal area proximate to keel and light yellow (2.5 Y 9/6) (near 2.5 Y 8/8), moderate yellow (near 2.5 Y 8/8), brilliant yellow (near 2.5 Y 8/8) and strong yellow (near 2.5 Y 8/8) in marginal and center field areas.

Androecium:

*Stamen number.*—Tube attached group: 97. Basally united group: 19.

*Filaments.*—Color: translucent white. Size: Length — Tube attached group: 56 mm (avg.). Basally united group: 49 mm (avg.). Diameter — About 0.35 mm intermediate the opposite ends.

*Anthers.*—Color (before dehiscing): Pale greenish yellow (10 Y 9/4).

Gynoecium (pistil):

*Style.*—Color: Strong reddish purple (2.5 RP 4/10) in basal area and deep reddish, purple (2.5 RP 3/10) in the distal area. Size (at full bloom): Length — 61 mm. Diameter — 2.0 mm intermediate opposite ends.

*Stigma.*—Color: light reddish purple (2.5 RP 6/8) and strong reddish purple (2.5 RP 5/10). Size: 5 mm (avg.) lobe length.

*Ovary.*—Color: Moderate yellow green (5 GY 5/6) and strong yellow green (5 GY 6/8). Size (at full bloom): Length (insertion to concavity base) — 10 mm. Major axis — 11 mm at distal end of concavity. Major axis — 9 mm at distal end of concavity.

We claim:

1. A new and distinct plant variety of the Cactaceae family as shown and described and which is mainly distinguished from its antecedents and known related varieties by a growth habit which is similar to that of the "Gold Charm" variety but as modified by the combination of the characteristics which follow:

(1) A more erect posture at maturity than the "Gold Charm" variety.

(2) Phylloclades which, in comparison to the "Gold Charm" variety, have (a) wings with generally greater thickness and width dimensions, and (b) teeth with generally greater thickness dimensions and in a larger number per phylloclade, (3) Flowers which, in comparison to the "Gold Charm" variety, are sterile and have (a) a sepaloid tepal series with generally shorter length dimensions, (b) a tube laminating tepal series that has a larger number of tepals, (c) a perianth tube that at the throat has a generally longer major elliptical axis dimension and a generally longer minor elliptical axis dimension, (d) an androecium with filaments of the tube attached stamen group that have shorter length dimensions, (e) a gynoecium that has a style with a generally shorter length dimension and generally larger diameter and ovaries with generally longer minor axis dimensions at the distal end of the concavity.

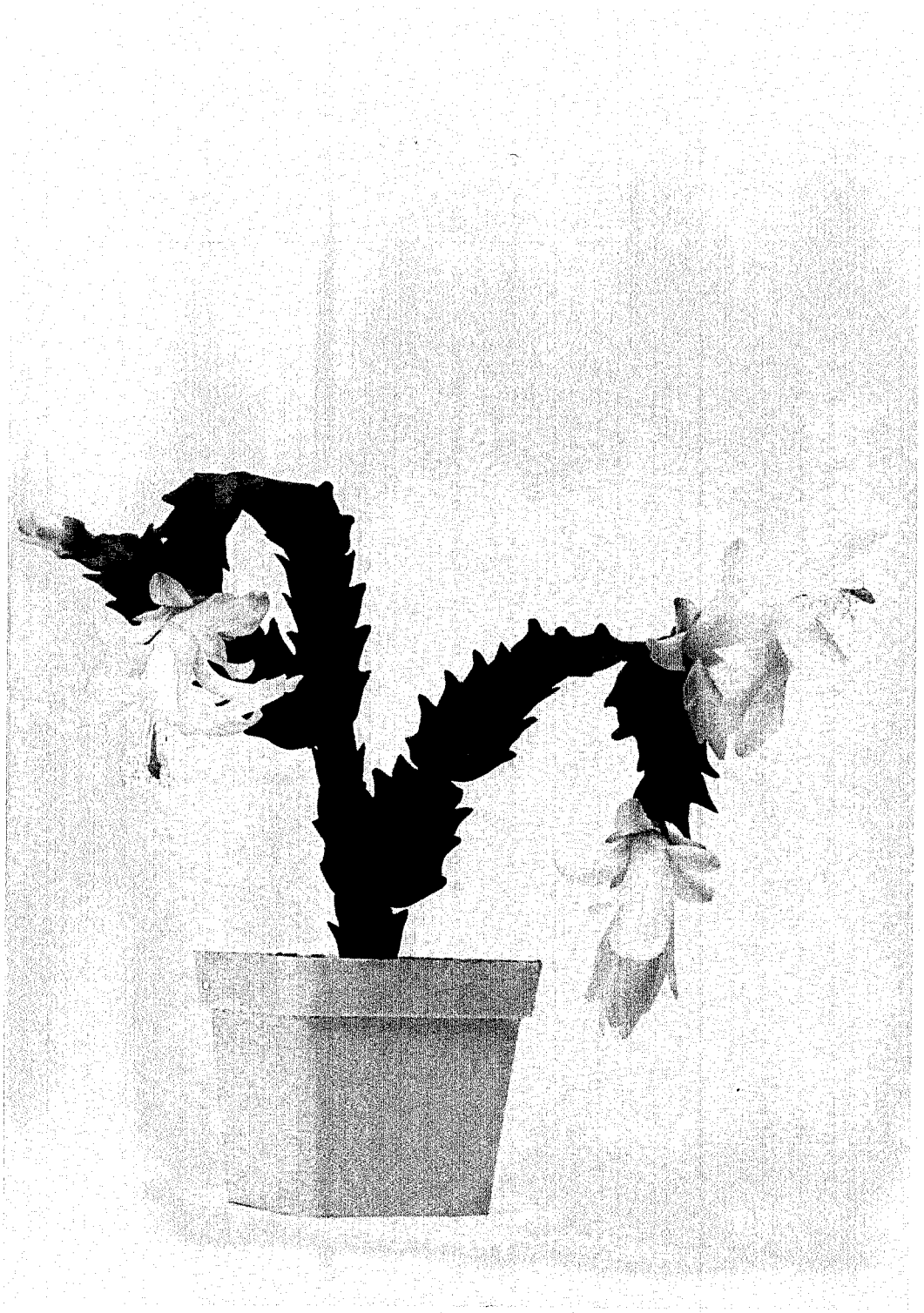

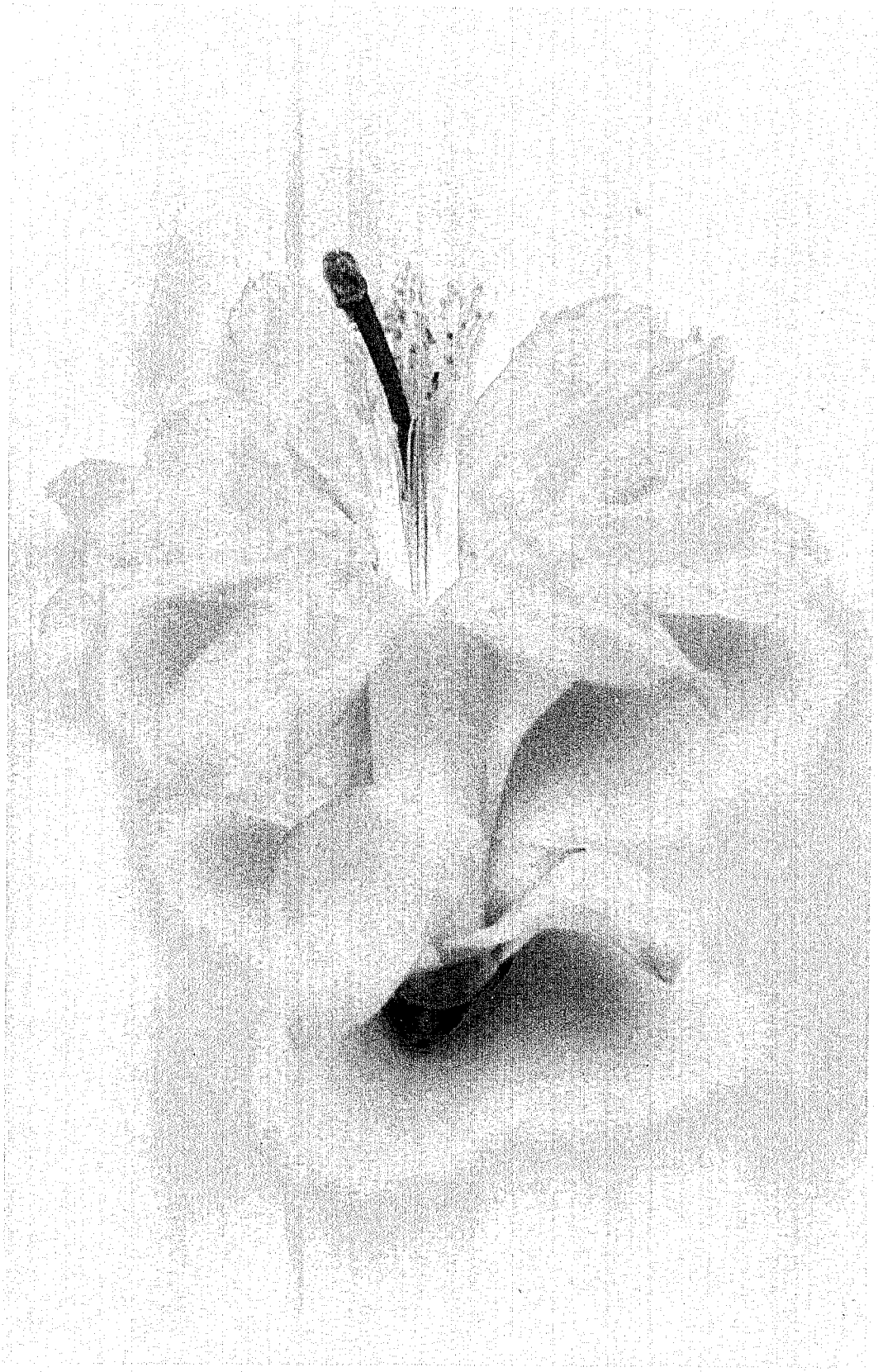

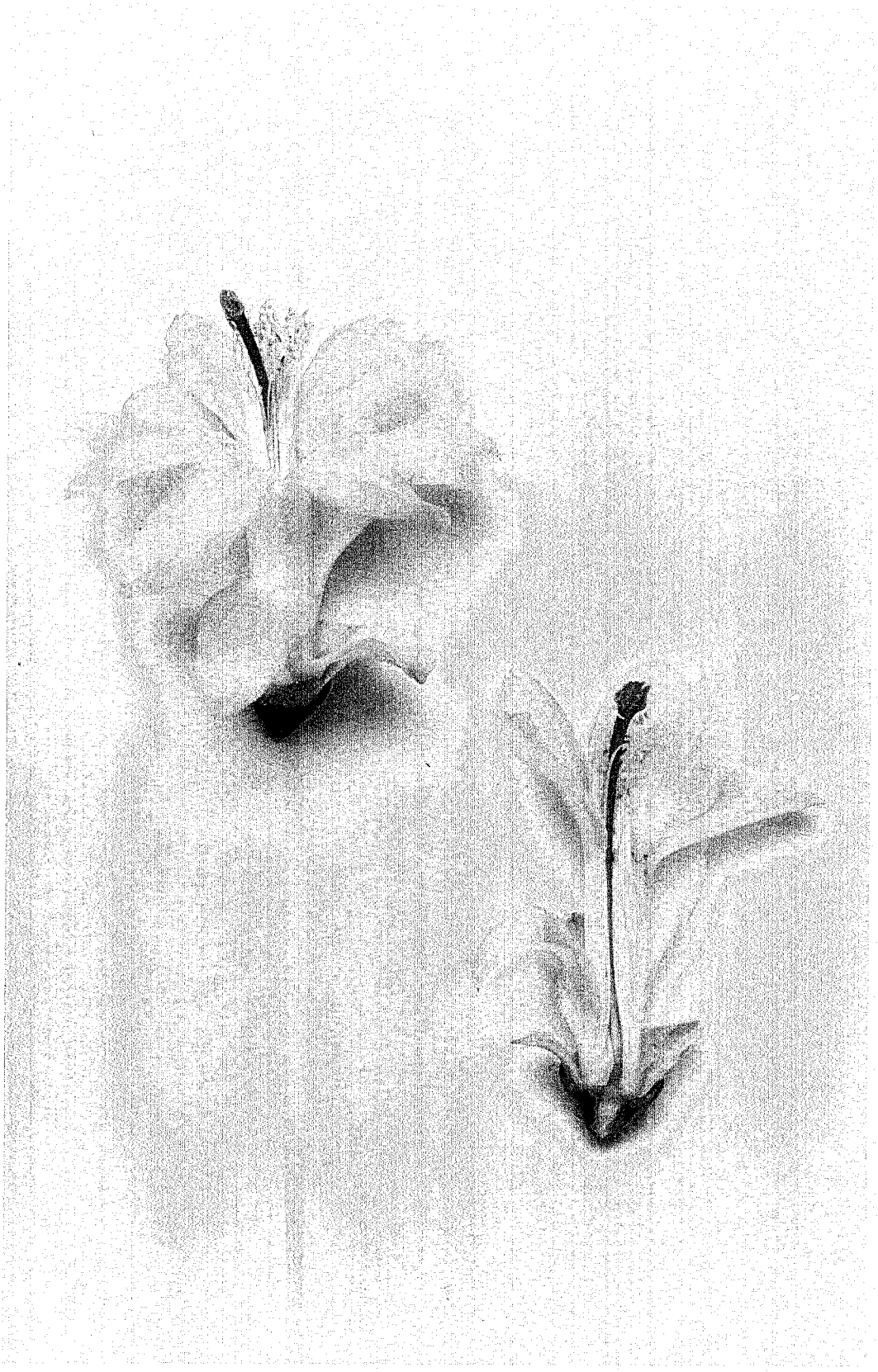

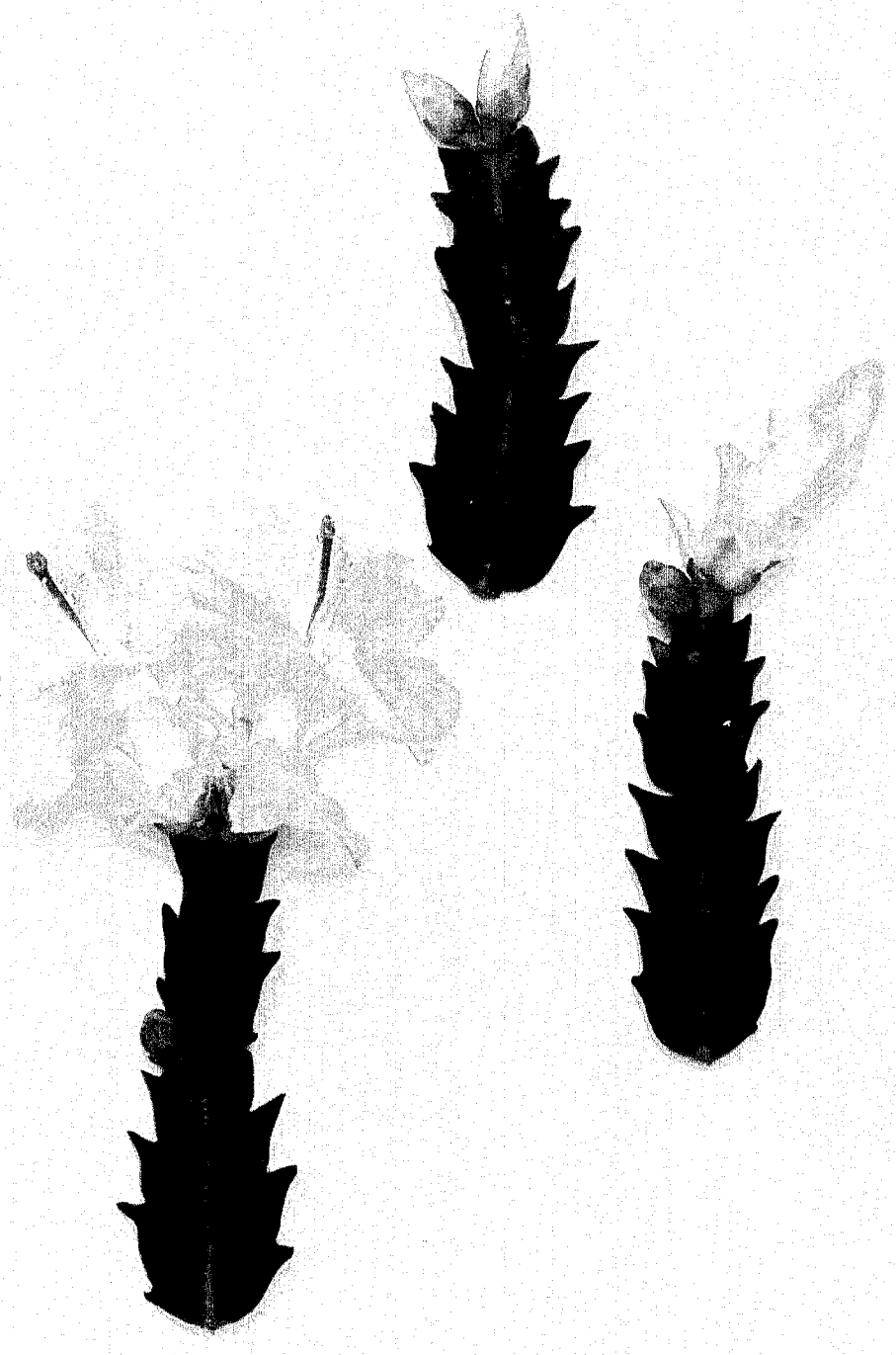

* * * * *